United States Patent [19]

Rentzea et al.

[11] Patent Number: 4,758,564
[45] Date of Patent: Jul. 19, 1988

[54] ETHER AND THIOETHER AMINES AND THEIR USE AS FUNGICIDES

[75] Inventors: Costin Rentzea, Heidelberg; Ernst Buschmann, Ludwigshafen; Norbert Goetz, Worms; Eberhard Ammermann, Ludwigshafen; Ernst-Heinrich Pommer, Limburgerhof, all of Fed. Rep. of Germany

[73] Assignee: BASF Aktiengesellschaft, Fed. Rep. of Germany

[21] Appl. No.: 830,108

[22] Filed: Feb. 18, 1986

[30] Foreign Application Priority Data

Feb. 22, 1985 [DE] Fed. Rep. of Germany ....... 3506117

[51] Int. Cl.$^4$ .................... A01N 43/84; C07D 265/30
[52] U.S. Cl. .................... 514/239.2; 514/212; 514/255; 514/315; 514/317; 514/428; 514/227.5; 540/609; 544/59; 544/158; 544/174; 544/177; 544/398; 546/236; 546/248; 548/574; 548/575
[58] Field of Search ............... 544/174, 177; 514/238

[56] References Cited

U.S. PATENT DOCUMENTS

| | | | |
|---|---|---|---|
| 2,105,828 | 1/1938 | Wilson | 544/170 |
| 2,567,351 | 9/1951 | Rievesehl | 544/174 |
| 2,812,327 | 11/1957 | Ohnacker et al. | 544/174 |
| 3,468,885 | 9/1969 | Sanne et al. | 544/178 |
| 3,472,845 | 10/1969 | Thiele | 544/174 |
| 3,478,096 | 11/1969 | Cyba | 260/563 |
| 3,651,067 | 3/1972 | Elpern et al. | 544/174 |
| 3,673,260 | 6/1972 | Esclamadon | 260/609 A |
| 3,790,569 | 2/1974 | Mauvernay et al. | 544/174 |
| 3,840,605 | 10/1974 | Gordon | 260/614 R |
| 3,891,709 | 6/1975 | Higuchi et al. | 260/584 B |
| 4,299,957 | 11/1981 | Brennan | 544/177 |
| 4,474,988 | 10/1984 | Kaiser | 564/508 |

FOREIGN PATENT DOCUMENTS

| | | |
|---|---|---|
| 162899 | 4/1949 | Fed. Rep. of Germany . |
| 193860 | 12/1957 | Fed. Rep. of Germany . |
| 267634 | 7/1950 | Switzerland . |
| 331991 | 9/1958 | Switzerland . |
| 1351505 | 5/1974 | United Kingdom . |
| 1352286 | 5/1974 | United Kingdom . |
| 1549123 | 7/1979 | United Kingdom . |
| 1590148 | 5/1981 | United Kingdom . |

OTHER PUBLICATIONS

Eprova Ltd., Chemical Abstracts, vol. 53 (1959) 18067c.

Primary Examiner—Richard L. Raymond
Attorney, Agent, or Firm—Keil & Weinkauf

[57] ABSTRACT

Amines of the general formula

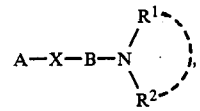

where A is alkyl, alkenyl, cycloalkyl, cycloalkenyl, phenylalkyl or phenylalkenyl, X is oxygen or sulfur, B is an alkylene chain and $R^1$ and $R^2$ are each alkyl, alkenyl or cycloalkyl, or $R^1$ and $R^2$ form part of a heterocyclic structrure, and their salts, as well as fungicides containing these compounds.

10 Claims, No Drawings

ETHER AND THIOETHER AMINES AND THEIR USE AS FUNGICIDES

The present invention relates to novel amines, processes for their preparation, their use as fungicides, fungicides which contain the novel active ingredients, processes for the preparation of such fungicidal mixtures, and methods of combating harmful fungi with these fungicides.

It has been disclosed that N-tridecyl-2,6-dimethylmorpholine and its salts (eg. the acetate) can be used as a fungicide (DE Nos. 1 164 152 and 1 173 722).

We have found that compounds of the formula I

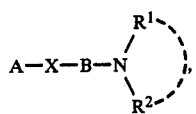

where A is unsubstituted or substituted alkyl, alkenyl, cycloalkyl, cycloalkenyl, phenylalkyl or phenylalkenyl, X is oxygen or sulfur, B is an alkylene chain of 2 to 10 carbon atoms which is unsubstituted or monosubstituted or polysubstituted by alkyl of 1 to 4 carbon atoms, and $R^1$ and $R^2$ are identical or different and independently of one another are each $C_1$–$C_{10}$-alkyl, $C_3$–$C_6$-alkenyl or $C_3$–$C_8$-cycloalkyl, or $R^1$ and $R^2$ as an alkylene group form part of a 5-membered, 6-membered or 7-membered heterocyclic structure which contains from 1 to 3 heteroatoms (nitrogen, oxygen or sulfur), does not possess a double bond in the ring and is unsubstituted or substituted by one or more, eg. 1 to 3, alkyl groups, each of which is of 1 to 4 carbon atoms, and their salts are very effective against harmful fungi and are very well tolerated by plants.

The novel amines of the formula I may contain chiral centers. They are generally obtained as racemates and may be obtained as diastereomer mixtures. In the case of some of the novel compounds, pure diastereomers can be isolated in pure form, for example by column chromatography or by virtue of solubility differences. Pure racemates and enantiomers can be obtained from such purified diastereomers by a conventional method. All these compounds and mixtures are embraced by the present invention. Regarding the use of the novel amines, the pure diastereomers and enantiomers as well as the mixtures of these obtained in the synthesis are suitable for use as fungicides. The said mixtures are preferably used.

A is, for example, $C_1$–$C_{19}$-alkyl, methyl, ethyl, straight-chain or branched propyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, halo-$C_1$–$C_{12}$-alkyl, chlorobutyl, chlorohexyl, fluoropentyl, fluorohexyl, fluoroheptyl, fluorodecyl, fluorododecyl, $C_2$–$C_{18}$-alkenyl, allyl, methallyl, pentenyl, hexenyl, heptenyl, octenyl, decenyl, dodecenyl, hexadecenyl, octadecenyl, halo-$C_2$–$C_4$-alkenyl, chloroallyl, bromoallyl, $C_3$–$C_{12}$-cycloalkyl, cyclopropyl, cyclopropylmethyl, cyclopentyl, methylcyclopentyl, cyclopentylmethyl, cyclohexyl, cyclohexylmethyl, cyclohexylethyl, cyclohexylpropyl, di-, tri- or tetramethylcyclohexyl, ethylcyclohexyl, propyl- or isopropylcyclohexyl, butyl, isobutyl, sec.-butyl- or tert.-butylcyclohexyl, tert.-amylcyclohexyl, cyclohexylcyclohexyl, menthyl, phenylcyclohexyl, cycloheptyl, cycloheptylmethyl, methylcycloheptyl, propylcycloheptyl, cyclooctyl, cyclododecyl, cyclododecylmethyl, $C_5$–$C_{12}$-cycloalkenyl, cyclopentenyl, campholenyl, cyclohexenylmethyl, tert.-butylcyclohexenyl, tert.-butylcyclohexylpropyl, tert.-butylcyclohexenylpropyl, cycloheptenyl, cyclooctenyl, cyclododecadienyl, cyclododecadienylmethyl, decalyl, norbornyl, tricyclodecanyl, 1,5-dimethylbicyclo[2.3.1]octan-8-yl, isobornyl, adamantyl, norbornylmethyl, camphenyl, homocamphenyl, pinanyl, norbornenyl, nopolyl, phenyl-$C_1$–$C_6$-alkyl, benzyl, halophenyl-$C_1$–$C_4$-alkyl, chlorobenzyl, fluorobenzyl, methylbenzyl, ethylbenzyl, propylbenzyl, butylbenzyl, methoxybenzyl, trifluoromethylbenzyl, phenylethyl, 1-(4-tert.-butylphenyl)-2-methylprop-3-yl, chlorophenylpropyl, dichlorophenylpropyl, fluorophenylpropyl, phenylpropyl, phenylbutyl, phenylpentyl, phenylhexyl, phenyl-$C_3$–$C_6$-alkenyl, phenylpropenyl, phenylbutenyl or phenylpentenyl.

$R^1$ and $R^2$ are each, for example, methyl, ethyl, straight-chain or branched propyl, butyl, pentyl, hexyl, heptyl, octyl, nonyl, decyl, allyl, methallyl, pentenyl, cyclopentyl, cyclohexyl, cyclohexylmethyl, methylcyclohexyl, tert.-butylcyclohexyl, cycloheptyl or cyclooctyl, or $R^1$ and $R^2$ together with the nitrogen atom on which they are substituents form a pyrrolidine, mono-, di- or trimethylpyrrolidine, piperidine, mono-, di- or trimethylpiperidine, ethylpiperidine, propylpiperidine, tert.-butylpiperidine, phenylpiperidine, morpholine, thiomorpholine, 2- or 3-methylmorpholine, 2,5-dimethylmorpholine, 2,6-dimethylmorpholine (cis-/trans or cis or trans), 2,6-dimethylthiomorpholine, piperazine, methyl-, ethyl-, propyl- or tert.-butylpiperazine or hexamethyleneimine radical.

The amines of the formula I can be prepared by a method in which (a) a compound of the formula II is reacted with an amine of the formula III

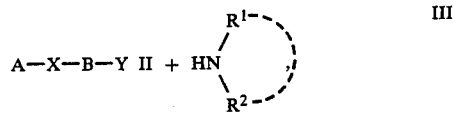

where A, X, B, $R^1$ and $R^2$ have the above meanings and Y is a nucleophilically displaceable leaving group, for example halogen (Cl, Br) or alkyl- or arylsulfonyl, or (b) an alkylating agent of the formula IV is reacted with an amine of the formula V

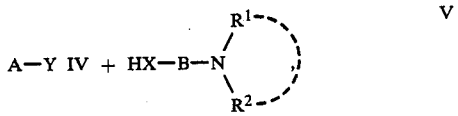

where A, B, X, Y, $R^1$ and $R^2$ have the above meanings, or (c) an alcohol or a thiol of the formula VI is reacted with an amine of the formula VII

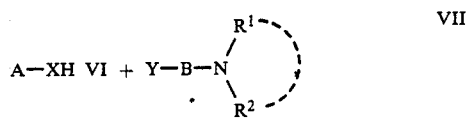

where A, B, X, Y, $R^1$ and $R^2$ have the above meanings, in the presence or absence of a solvent or diluent and/or of an inorganic or organic base and/or of a reaction accelerator, and, if required, the resulting compound is converted to its salts.

Examples of suitable solvents or diluents for all three versions (a), (b) and (c) of the process are halohydrocarbons, in particular chlorohydrocarbons, eg. tetrachloroethylene, 1,1,2,2- or 1,1,1,2-tetrachloroethane, dichloropropane, methylene chloride, dichlorobutane, chloroform, chloronaphthalene, dichloronaphthalene, carbon tetrachloride, 1,1,1- or 1,1,2-trichloroethane, trichloroethylene, pentachloroethane, o-, m- and p-difluorobenzene, 1,2-dichloroethane, 1,1-dichloroethane, 1,2-cis-dichloroethylene, chlorobenzene, fluorobenzene, bromobenzene, iodobenzene, o-, m- and p-dichlorobenzene, o-, p- and m-dibromobenzene, o-, m- and p-chlorotoluene and 1,2,4-trichlorobenzene; ethers, eg. ethyl propyl ether, methyl tert.-butyl ether, n-butyl ethyl ether, di-n-butyl ether, diisobutyl ether, diisoamyl ether, diisopropyl ether, anisole, phenetole, cyclohexyl methyl ether, diethyl ether, ethylene glycol dimethyl ether, tetrahydrofuran, dioxane, thioanisole and $\beta,\beta'$-dichlorodiethyl ether; nitrohydrocarbons, such as nitromethane, nitroethane, nitrobenzene, o-, m- and p-chloronitrobenzene and o-nitrotoluene; nitriles, such as acetonitrile, butyronitrile, isobutyronitrile, benzonitrile and m-chlorobenzonitrile; aliphatic and cycloaliphatic hydrocarbons, eg. heptane, pinane, nonane, o-, m- and p-cymene, gasoline fractions boiling within a range from 70° to 190° C., cyclohexane, methylcyclohexane, decalin, petroleum ether, hexane, naphtha, 2,2,4-trimethylpentane, 2,2,3-trimethylpentane, 2,3,3-trimethylpentane and octane; esters, eg. ethyl acetate, ethyl acetoacetate and isobutyl acetate; amides, eg. formamide, methylformamide and dimethylformamide; ketones, eg. acetone, methyl ethyl ketone, and, if appropriate, water and mixtures of these. The compounds of the formulae III, IV and V in excess may also be used as solvents. Advantageously, the solvent is used in an amount of from 100 to 2,000, preferably from 200 to 700, % by weight, based on starting material II.

All conventional acid acceptors can be used as inorganic or organic bases for the conversion to compounds of the formula I. These preferably include tertiary amines, alkaline earth metal compounds, ammonium compounds and alkali metal compounds, as well as mixtures of these. However, it is also possible to use zinc compounds. Examples of suitable basic compounds are potassium hydroxide, sodium hydroxide, potassium carbonate, sodium carbonate, lithium hydroxide, lithium carbonate, sodium bicarbonate, potassium bicarbonate, calcium hydroxide, calcium oxide, barium oxide, magnesium hydroxide, magnesium oxide, barium hydroxide, calcium carbonate, magnesium carbonate, magnesium bicarbonate, magnesium acetate, zinc hydroxide, zinc oxide, zinc carbonate, zinc bicarbonate, zinc acetate, sodium formate, sodium acetate, trimethylamine, triethylamine, tripropylamine, triisopropylamine, tributylamine, triisobutylamine, tri-sec.-butylamine, tri-tert.-butylamine, tribenzylamine, tricyclohexylamine, triamylamine, trihexylamine, N,N-dimethylaniline, N,N-diethylaniline, N,N-dipropylaniline, N,N-dimethyltoluidine, N,N-diethyltoluidine, N,N-dipropyltoluidine, N,N-dimethyl-p-aminopyridine, N,N-diethyl-p-aminopyridine, N,N-dipropyl-p-aminopyridine, N-methylpyrrolidine, N-ethylpyrrolidone, N-methylpiperidine, N-ethylpiperidine, N-methylpyrrolidine, N-ethylpyrrolidine, N-methylimidazole, N-ethylimidazole, N-methylpyrrole, N-ethylpyrrole, N-methylmorpholine, N-ethylmorpholine, N-methylhexamethyleneimine, N-ethylhexamethyleneimine, pyridine, quinoline, alpha-picoline, $\beta$-picoline, gamma-picoline, isoquinoline, pyrimidine, acridine, N,N,N',N'-tetramethylethylenediamine, N,N,N',N'-tetraethylethylenediamine, quinoxaline, quinazoline, N-propyldiisopropylamine, N,N-dimethylcyclohexylamine, 2,6-lutidine, 2,4-lutidine, trifurfurylamine and triethylenediamine.

Advantageously, the acid acceptor is used in an amount of from 0.8 to 1.2 moles per mole of starting material II, IV or VI.

Preferred reaction accelerators are metal halides, such as sodium iodide or potassium iodide.

For salt formation with compounds of the formula I, all organic and inorganic acids are suitable, provided that they form salts which are physiologically tolerated by plants. Examples are chlorides, bromides, iodides, sulfates, phosphates, acetates, oxalates, fumarates, malonates, alkylsulfonates and arylsulfonates.

The salts are obtained by combining the appropriate acid with the free amine of the formula I in the presence or absence of an inert solvent, separating off the solvent and, if required, recrystallizing the residue.

The starting materials of the formula II, where Y is chlorine or bromine, are novel and also form a subject of the invention. They can be prepared by conventional methods.

They can be obtained, for example, by the reaction (d) of an alcohol or thiol of the formula IV $$A-XH \qquad\qquad IV$$

where A and X have the above meanings, with a 1, omegadihalo derivative of the formula VIII $$Y-B-Y \qquad\qquad VIII$$

where B and Y have the above meanings, in the presence or absence of one or more solvents and diluents and/or inorganic bases and/or a phase transfer catalyst.

Reaction (d) is advantageously carried out in a solvent which is inert to the reactants, eg. toluene, xylene, 1,2-dimethoxyethane, tetrahydrofuran, dioxane, methylene chloride, dimethylformamide, water or a mixture of these. The compounds of the formula VIII in excess may also be used as solvents.

Examples of suitable acid acceptors are inorganic bases such as hydrides, hydroxides, carbonates, borates or phosphates of alkali metals and alkaline earth metals, eg. sodium hydride, sodium hydroxide, potassium hydroxide, calcium oxide, sodium carbonate, potassium carbonate, sodium bicarbonate, potassium bicarbonate, magnesium carbonate, calcium carbonate, barium carbonate, sodium phosphates and potassium phosphates.

Preferred phase transfer catalysts are quaternary ammonium and phosphonium salts, such as tetrabutylammonium chloride, bisulfate, hydroxide, bromide or iodide, benzyltriethylammonium chloride, cetyltrimethylammonium chloride or benzyltriphenylphosphonium chloride, and crown ethers, such as 12-crown-4, 15-crown-5, 18-crown-6, dibenzo-18-crown-6 or dicyclohexano-18-crown-6.

Reactions (a), (b), (c) and (d) are generally carried out at from 0° to 100° C., under atmospheric or superatmospheric pressure, continuously or batchwise.

Intermediates, for example the alkylating agents IV, the amines III, V and VII, and the alcohols or thiols VI, are well known.

METHOD 1

Preparation of the intermediate

A vigorously stirred mixture of 130 g (1 mole) of 2-ethyl-4-methylpentan-1-ol, 500 ml of 1,5-dichloropentane, 15 g of tetrabutylammonium bisulfate and 250 g of 50% strength by weight aqueous sodium hydroxide solution is heated at 50° C. for 24 hours, after which 1 l of water is added and the mixture is extracted with four times 300 ml of methylene chloride. The combined extracts are extracted by shaking with five times 200 ml of water, dried over magnesium sulfate and subjected to fractional distillation under reduced pressure.

180 g (77% of theory) of 1-(2-ethyl-4-methyl-pent-1-yl)-5-chloropentane are obtained as a colorless liquid of boiling point 90°–92° C. under 0.3 mbar and $n_D^{22}$ 1.4488.

The following intermediates of the formula A-X-B-Y can be prepared in a similar manner:

| A | X | B | Y | Refractive index or bp. [°C./mbar] |
|---|---|---|---|---|
| n-Propyl | O | $(CH_2)_4$ | Cl | 84–86/27 |
| Isopropyl | O | $(CH_2)_4$ | Cl | 83–84/27 |
| n-Butyl | O | $(CH_2)_4$ | Cl | $n_D^{25}$ = 1.4310 |
| Isobutyl | O | $(CH_2)_4$ | Cl | 92–94/28 |
| n-Butyl | O | $(CH_2)_6$ | Cl | 98–100/27 |
| n-Hexyl | O | $(CH_2)_4$ | Cl | 122–124/30 |
| 1-Chlorhex-6-yl | O | $(CH_2)_6$ | Cl | $n_D^{22}$ = 1.4485 |
| 2,2-Dimethylprop-1-yl | O | $(CH_2)_4$ | Cl | 97–98/27 |
| 2,2-Dimethylprop-1-yl | O | $(CH_2)_6$ | Cl | 122–125/30 |
| 3,3-Dimethylbut-1-yl | O | $(CH_2)_4$ | Cl | $n_D^{25}$ = 1.4355 |
| 3,3-Dimethylbut-1-yl | O | $(CH_2)_6$ | Cl | $n_D^{22}$ = 1.4400 |
| 2,4-Dimethylpent-1-yl | O | $(CH_2)_4$ | Cl | $n_D^{22}$ = 1.4360 |
| 2,4-Dimethylpent-1-yl | O | $(CH_2)_6$ | Cl | $n_D^{22}$ = 1.4419 |
| 2-Ethyl-4-methylpent-1-yl | O | $(CH_2)_3$ | Cl | $n_D^{26}$ = 1.4557 |
| 2-Ethyl-4-methylpent-1-yl | O | $(CH_2)_4$ | Cl | $n_D^{25}$ = 1.4390 |
| 2-Ethyl-4-methylpent-1-yl | O | $(CH_2)_6$ | Cl | $n_D^{22}$ = 1.4590 |
| 5-Ethylhept-2-yl | O | $(CH_2)_4$ | Cl | $n_D^{22}$ = 1.4442 |
| 5-Ethylhept-2-yl | O | $(CH_2)_6$ | Cl | $n_D^{22}$ = 1.4485 |
| 2-Ethylhex-1-yl | O | $(CH_2)_3$ | Cl | $n_D^{22}$ = 1.4336 |
| 2-Ethylhex-1-yl | O | $(CH_2)_4$ | Cl | $n_D^{21}$ = 1.4420 |
| 2-Ethylhex-1-yl | O | $(CH_2)_5$ | Cl | $n_D^{22}$ = 1.4444 |
| 2-Ethylhex-1-yl | O | $(CH_2)_6$ | Cl | $n_D^{25}$ = 1.4456 |
| 2-Ethylhex-1-yl | O | $CH_2CHCH_2$<br>$\|$<br>$CH_3$ | Cl | 95–97/30 |
| 2-Ethylhex-1-yl | O | $(CH_2)_8$ | Cl | 133–135/0,3 |
| n-Octyl | O | $(CH_2)_4$ | Cl | $n_D^{21}$ = 1.4418 |
| n-Nonyl | O | $(CH_2)_4$ | Cl | $n_D^{21}$ = 1.4438 |
| n-Undecyl | O | $(CH_2)_4$ | Cl | $n_D^{22}$ = 1.4458 |
| 5-Methyl-2-isopropyl-hex-1-yl | O | $(CH_2)_4$ | Cl | $n_D^{25}$ = 1.4445 |
| 3-Methylhept-2-yl | O | $(CH_2)_4$ | Cl | $n_D^{22}$ = 1.4412 |
| 3,5,5-Trimethylhex-1-yl | O | $(CH_2)_4$ | Cl | $n_D^{25}$ = 1.4430 |
| 3,7-Dimethyloct-1-yl | O | $(CH_2)_4$ | Cl | $n_D^{25}$ = 1.4475 |
| 3,7-Dimethyloct-1-yl | O | $(CH_2)_4$ | Cl | $n_D^{25}$ = 1.4500 |
| 2-(n-Butyl)-oct-1-yl | O | $(CH_2)_4$ | Cl | $n_D^{25}$ = 1.4472 |
| 2-(n-Butyl)-oct-1-yl | O | $(CH_2)_5$ | Cl | $n_D^{22}$ = 1.4482 |
| 2-(n-Butyl)-oct-1-yl | O | $(CH_2)_6$ | Cl | $n_D^{22}$ = 1.4508 |
| 2-(n-Butyl)-oct-1-yl | O | $(CH_2)_3$ | Cl | $n_D^{22}$ = 1.4450 |
| $CF_3CH_2CF_2CH_2-$ | O | $(CH_2)_4$ | Cl | 98–100/30 |
| $CF_2H-CF_2CH_2-$ | O | $(CH_2)_4$ | Cl | 86–88/27 |
| $CF_3(CF_2)_9CH_2CH_2-$ | O | $(CH_2)_4$ | Cl | 116–120/0.3 |
| $CF_3(CF_2)_9CH_2CH_2-$ | O | $(CH_2)_4$ | Cl | 125–127/0.3 |
| 3,7,11-Trimethyldodec-1-yl | O | $(CH_2)_4$ | Cl | $n_D^{22}$ = 1.4523 |
| 3,7,11-Trimethyldodec-1-yl | O | $(CH_2)_6$ | Cl | $n_D^{25}$ = 1.4545 |
| 2-(n-Hexyl)-decyl-1 | O | $(CH_2)_4$ | Cl | $n_D^{22}$ = 1.4520 |
| 2-(1,3,3-Trimethylbutyl-1)-5,7,7-trimethyloct-1-yl | O | $(CH_2)_4$ | Cl | $n_D^{22}$ = 1.4546 |
| Cyclopropylmethyl | O | $(CH_2)_6$ | Br | $n_D^{22}$ = 1.4122 |
| Cyclopentyl | O | $(CH_2)_4$ | Cl | $n_D^{20}$ = 1.4607 |
| Cyclohexyl | O | $(CH_2)_4$ | Cl | $n_D^{20}$ = 1.4660 |
| Cyclohexylmethyl | O | $(CH_2)_4$ | Cl | 120–122/30 |
| 4-Methylcyclohexyl | O | $(CH_2)_4$ | Cl | 124–126/29 |
| 2-(Cyclohexyl)-prop-1-yl | O | $(CH_2)_4$ | Cl | 106–10 8/0.3 |
| 3,5,5-Trimethylcyclohexyl | O | $(CH_2)_4$ | Cl | $n_D^{22}$ = 1.4607 |
| 3,5,5-Trimethylcyclohexyl | O | $(CH_2)_5$ | Cl | 84–86/0.3 |
| 3,5,5-Trimethylcyclohexyl | O | $(CH_2)_6$ | Cl | 92–94/0.4 |
| 4-tert.-Butylcyclohexyl | O | $(CH_2)_4$ | Cl | $n_D^{22}$ = 1.4685 |
| 4-tert.-Butylcyclohexyl | O | $(CH_2)_5$ | Cl | $n_D^{25}$ = 1.4692 |
| 4-tert.-Butylcyclohexyl | O | $(CH_2)_6$ | Cl | $n_D^{22}$ = 1.4675 |
| Menthyl | O | $(CH_2)_4$ | Cl | 85–90/0.2 |
| Menthyl | O | $(CH_2)_6$ | Cl | 90–92/0.3 |
| Cycloheptyl | O | $(CH_2)_4$ | Cl | $n_D^{20}$ = 1.4735 |
| 3,3-Dimethyl-2,4-endomethylen cyclohexylmethyl | O | $(CH_2)_4$ | Cl | $n_D^{22}$ = 1.4789 |

-continued

| A | X | B | Y | Refractive index or bp. [°C./mbar] |
|---|---|---|---|---|
| 4-tert.-Amylcyclohexyl | O | (CH$_2$)$_4$ | Cl | $n_D^{22}$ = 1.4715 |
| 4-tert.-Amylcyclohexyl | O | (CH$_2$)$_6$ | Cl | $n_D^{22}$ = 1.4722 |
| 2-(2,2,3-Trimethylcyclopent-3-en-1-yl)-eth-1-yl | O | (CH$_2$)$_4$ | Cl | 82–84/0.3 |
| 2-(2,2-Dimethyl-3,6-endomethylen-cyclohexyl)-eth-1-yl | O | (CH$_2$)$_4$ | Cl | 90–92/0.2 |
| Isobornyl | O | (CH$_2$)$_4$ | Cl | 88–89/0.3 |
| Norbornyl | O | (CH$_2$)$_4$ | Cl | $n_D^{22}$ = 1.4775 |
| Norbornyl | O | (CH$_2$)$_6$ | Cl | $n_D^{22}$ = 1.4780 |
| Cyclododecyl | O | (CH$_2$)$_4$ | Cl | $n_D^{24}$ = 1.4824 |
| Allyl | O | (CH$_2$)$_4$ | Cl | 84–86/27 |
| Allyl | O | (CH$_2$)$_6$ | Cl | 88–90/28 |
| Methallyl | O | (CH$_2$)$_4$ | Cl | 87–89/28 |
| 2-Buten-1-yl | O | (CH$_2$)$_4$ | Cl | 87–88/28 |
| 3-Methylbut-2-en-1-yl | O | (CH$_2$)$_4$ | Cl | 92–94/30 |
| Geranyl | O | (CH$_2$)$_4$ | Cl | 78–82/0.3 |
| Phytyl | O | (CH$_2$)$_4$ | Cl | 120–123/0.2 |
| Octadec-9-en-1-yl | O | (CH$_2$)$_4$ | Cl | $n_D^{21}$ = 1.4625 |
| 3-Chlorallyl | O | (CH$_2$)$_4$ | Cl | 87–89/27 |
| 2-Chlorallyl | O | (CH$_2$)$_4$ | Cl | 80–82/28 |
| 2,3,3-Trichlorallyl | O | (CH$_2$)$_4$ | Cl | $n_D^{22}$ = 1.5040 |
| 2,3,3-Trichlorallyl | O | (CH$_2$)$_6$ | Cl | $n_D^{22}$ = 1.5080 |
| Benzyl | O | (CH$_2$)$_4$ | Cl | 118–120/28 |
| 4-Methylbenzyl | O | (CH$_2$)$_4$ | Cl | 121–123/27 |
| 4-Fluorbenzyl | O | (CH$_2$)$_4$ | Cl | 117–119/30 |
| 4-Chlorbenzyl | O | (CH$_2$)$_4$ | Cl | 130–132/27 |
| 4-tert.-Butylbenzyl | O | (CH$_2$)$_4$ | Cl | 110–112/0.2 |
| 4-Methoxybenzyl | O | (CH$_2$)$_4$ | Cl | 98–99/0.4 |
| 4-Isopropylbenzyl | O | (CH$_2$)$_4$ | Cl | 102–104/0.2 |
| 2-(4-Methylphenyl)-ether | O | (CH$_2$)$_4$ | Cl | $n_D^{22}$ = 1.5061 |
| 3-Phenylprop-1-yl | O | (CH$_2$)$_4$ | Cl | $n_D^{22}$ = 1.5043 |
| 3-Phenylprop-1-yl | O | (CH$_2$)$_6$ | Cl | $n_D^{25}$ = 1.4995 |
| 3-Phenyl-2-methylprop-1-yl | O | (CH$_2$)$_4$ | Cl | $n_D^{22}$ = 1.5005 |
| 3-Phenyl-2-methylprop-1-yl | O | (CH$_2$)$_6$ | Cl | $n_D^{25}$ = 1.4961 |
| 3-(4-Isopropylphenyl)-2-methylprop-1-yl | O | (CH$_2$)$_6$ | Cl | $n_D^{22}$ = 1.4934 |
| 3-(4-tert.-Butylphenyl)-2-methylprop-1-yl | O | (CH$_2$)$_3$ | Cl | 149–151/0.2 |
| 3-(4-tert.-Butylphenyl)-2-methylprop-1-yl | O | (CH$_2$)$_4$ | Cl | 155–157/0.2 |
| 3-(4-tert.-Butylphenyl)-2-methylprop-1-yl | O | (CH$_2$)$_5$ | Cl | $n_D^{22}$ = 1.4962 |
| 3-(4-tert.-Butylphenyl)-2-methylprop-1-yl | O | (CH$_2$)$_6$ | Cl | $n_D^{25}$ = 1.4945 |
| 3-(4-tert.-Butylphenyl)-2-methylprop-1-yl | O | (CH$_2$)$_8$ | Cl | $n_D^{22}$ = 1.4927 |
| 5-Phenyl-2,4-dimethylpent-1-yl | O | (CH$_2$)$_4$ | Cl | $n_D^{22}$ = 1.4972 |
| 5-Phenyl-2,4-dimethylpent-1-yl | O | (CH$_2$)$_6$ | Cl | $n_D^{22}$ = 1.4944 |

EXAMPLE 1

A stirred mixture of 41.1 g (0.15 mole) of 4-(cyclododecyloxy)-1-chlorobutane, 120 ml of cis-2,6-dimethylmorpholine and 3 g of potassium iodide was heated at 90° C. for 24 hours. The reaction mixture was cooled to 10° C., after which 100 ml of petroleum ether and 70 ml of 20% strength aqueous sodium hydroxide solution were added in succession. The organic phase was washed with three times 80 ml of water, dried over Na$_2$SO$_4$ and subjected to fractional distillation under reduced pressure.

46.8 g (88.4% of theory) of N-(cyclododecyloxybutyl)-cis-2,6-dimethylmorpholine were obtained as a colorless oil of boiling point 181°–182° C./0.15 mbar and $n_D^{22}$=1.4832.

EXAMPLE 2

A thoroughly stirred mixture of 42 g (0.12 mol) of N-(3-hydroxy-2-methylprop-1-yl)-2,6-dimethylmorpholine, 100 ml of 2-ethylhexyl chloride, 4 g of tetrabutylammonium chloride and 70 g of 50% strength aqueous sodium hydroxide solution was heated at 50° C. for 72 hours. Thereafter, 200 ml of water were added to the mixture, which was then extracted with three times 100 ml of methylene chloride. The combined extracts were washed with five times 80 ml of water, dried over sodium sulfate and fractionated under reduced pressure.

6.2 g (17.3% of theory) of N-[3-(2-ethylhexyloxy)-2-methylprop-1-yl]-2,6-dimethylmorpholine were obtained as a colorless oil of boiling point 130° C./0.1 mbar and $n_D^{22}$=1.4504.

EXAMPLE 3

66.5 g (0.46 mole) of 3,5,5-trimethylhexanol, 19 g (0.092 mole) of N-(3-chloro-2-methylprop-1-yl)-2,6-dimethylmorpholine, 2 g of tetrabutylammonium bisulfate and 65 g of 50% strength aqueous sodium hydroxide solution were reacted at 50° C. for 72 hours by a procedure similar to that described in Example 2.

15 g (52.1% of theory) of N-[3-(3,5,5-trimethylhexyloxy)-2-methylprop-1-yl]-2,6-dimethylmorpholine were obtained as a colorless liquid of boiling point 135° C./0.2 mbar and $n_D^{22}$=1.4486.

EXAMPLE 4

20.2 g (0.1 mole) of n-dodecylmercaptan were added dropwise to a stirred suspension of 3.2 g (0.13 mole) of sodium hydride in 120 ml of dry dimethylformamide at from 20° to 25° C. in a dry nitrogen atmosphere. The mixture was stirred for two hours at 20° C., after which 19.2 g (0.1 mole) of N-(3-chloroprop-1-yl)-2,6-dimethylmorpholine were added dropwise and the reaction mixture was stirred for a further 16 hours. 40 ml of ice water were carefully added dropwise, and the mixture was evaporated down under reduced pressure. The residue was partitioned between 300 ml of ether and 80 ml of water, and the organic phase was washed with twice 100 ml of water, dried over $Na_2SO_4$ and evaporated down. The residue was distilled under reduced pressure.

29.5 g (82.6% of theory) of N-[3-(n-dodecylthio)-prop-1-yl]-2,6-dimethylmorpholine were obtained as a colorless oil of boiling point 175°–176° C./0.05 mbar and $n_D^{22}$=1.4772.

The compounds listed below can be obtained in a similar manner by suitable choice of the starting materials and appropriate adaptation of the process conditions.

| Example No. | A | X | B | $R^1$ | $R^2$ | Refractive index or bp. [°C./mbar] |
|---|---|---|---|---|---|---|
| 5 | n-propyl | O | $(CH_2)_4$ | ethyl | ethyl | 86–88/0.5 |
| 6 | isopropyl | O | $(CH_2)_4$ | n-propyl | n-propyl | 91–93/0.4 |
| 7 | n-butyl | O | $(CH_2)_4$ | —$CH_2$—$CH(CH_3)OCH(CH_3)CH_2$— | | $n_D^{25}$ = 1.4485 |
| 8 | n-butyl | O | $(CH_2)_4$ | —$(CH_2)_2N(CH_3)(CH_2)_2$— | | 98–100/0.4 |
| 9 | isobutyl | O | $(CH_2)_4$ | —$(CH_2)_4$— | | 88–90/0.3 |
| 10 | isobutyl | O | $(CH_2)_6$ | —$(CH_2)_4$— | | 92–94/0.3 |
| 11 | n-hexyl | O | $(CH_2)_4$ | —$CH_2$—$CH(CH_3)OCH(CH_3)CH_2$— | | $n_D^{25}$ = 1.4505 |
| 12 | n-hexyl | O | $(CH_2)_4$ | —$(CH_2)_5$— | | 118–120/0.3 |
| 13 | n-hexyl | O | $(CH_2)_4$ | —$(CH_2)_2N(CH_3)(CH_2)_2$— | | 120–123/0.4 |
| 14 | 2,2-dimethylprop-1-yl | O | $(CH_2)_6$ | —$CH_2$—$CH(CH_3)OCH(CH_3)CH_2$— | | $n_D^{22}$ = 1.4465 |
| 15 | 2,2-dimethylprop-1-yl | O | $(CH_2)_6$ | —$CH_2$—$CH(CH_3)OCH(CH_3)CH_2$— | | |
| 16 | 2,2-dimethylprop-1-yl | O | $(CH_2)_6$ | —$(CH_2)_2N(CH_3)(CH_2)_2$— | | 114–116/0.4 |
| 17 | 3,3-dimethylbut-1-yl | O | $(CH_2)_4$ | —$CH_2$—$CH(CH_3)OCH(CH_3)CH_2$— | | $n_D^{22}$ = 1.4490 |
| 18 | 3,3-dimethylbut-1-yl | O | $(CH_2)_6$ | —$CH_2$—$CH(CH_3)OCH(CH_3)CH_2$— | | $n_D^{22}$ = 1.4510 |
| 19 | 3,3-dimethylbut-1-yl | O | $(CH_2)_4$ | —$(CH_2)_2N(CH_3)(CH_2)_2$— | | 104–106/0.4 |
| 20 | 3,3-dimethylbut-1-yl | O | $(CH_2)_6$ | —$(CH_2)_2N(CH_3)(CH_2)_2$— | | 129–132/0.4 |
| 21 | 2,4-dimethylpent-1-yl | O | $(CH_2)_4$ | —$(CH_2)_2N(CH_3)(CH_2)_2$— | | 110–113/0.3 |
| 22 | 2,4-dimethylpent-1-yl | O | $(CH_2)_4$ | —$CH_2$—$CH(CH_3)OCH(CH_3)CH_2$— | | $n_D^{22}$ = 1.4511 |
| 23 | 2,4-dimethylpent-1-yl | O | $(CH_2)_6$ | —$CH_2$—$CH(CH_3)OCH(CH_3)CH_2$— | | $n_D^{22}$ = 1.4520 |
| 24 | 2-ethyl-4-methylpent-1-yl | O | $(CH_2)_3$ | —$CH_2$—$CH(CH_3)OCH(CH_3)CH_2$— | | $n_D^{22}$ = 1.4502 |
| 25 | 2-ethyl-4-methylpent-1-yl | O | —$CH_2$—$CH(CH_3)CH_2$— | —$CH_2$—$CH(CH_3)OCH(CH_3)CH_2$— | | $n_D^{22}$ = 1.4491 |
| 26 | 2-ethyl-4-methylpent-1-yl | O | $(CH_2)_4$ | —$CH_2$—$CH(CH_3)OCH(CH_3)CH_2$— | | $n_D^{25}$ = 1.4510 |
| 27 | 2-ethyl-4-methylpent-1-yl | O | $(CH_2)_5$ | —$CH_2$—$CH(CH_3)OCH(CH_3)CH_2$— | | $n_D^{22}$ = 1.4532 |
| 28 | 2-ethyl-4-methylpent-1-yl | O | $(CH_2)_6$ | —$CH_2$—$CH(CH_3)OCH(CH_3)CH_2$— | | 141–143/0.3 |
| 29 | 2-ethyl-4-methylpent-1-yl | O | $(CH_2)_4$ | —$(CH_2)_4$—$CH(CH_3)$— | | $n_D^{22}$ = 1.4589 |
| 30 | 2-ethyl-4-methylpent-1-yl | O | $(CH_2)_4$ | —$(CH_2)_3$—$CH(CH_3)CH_2$— | | $n_D^{22}$ = 1.4563 |
| 31 | 2-ethyl-4-methylpent-1-yl | O | $(CH_2)_4$ | —$CH_2CH(CH_3)CH_2CH(CH_3)CH_2$— | | $n_D^{22}$ = 1.4529 |
| 32 | 2-ethyl-4-methylpent-1-yl | O | $(CH_2)_4$ | allyl | allyl | |
| 33 | 2-ethyl-4-methylpent-1-yl | O | $(CH_2)_4$ | allyl | n-propyl | |
| 34 | 2-ethyl-4-methylpent-1-yl | O | $(CH_2)_4$ | methyl | 2-ethylhex-1-yl | |
| 35 | 2-ethyl-4-methylpent-1-yl | O | $(CH_2)_4$ | ethyl | n-decyl | |
| 36 | 2-ethyl-4-methylpent-1-yl | O | $(CH_2)_4$ | n-hexyl | cycloheptyl | |
| 37 | 2-ethyl-4-methylpent-1-yl | O | $(CH_2)_4$ | methyl | cycloheptyl | |
| 38 | n-octyl | O | $(CH_2)_4$ | —$CH_2CH(CH_3)OCH(CH_3)CH_2$— | | $n_D^{22}$ = 1.4519 |
| 39 | n-octyl | O | $(CH_2)_4$ | —$(CH_2)_2M(CH_2)_2$— | | 130–132/0.3 |
| 40 | n-nonyl | O | $(CH_2)_4$ | —$CH_2$—$CH(CH_3)O$—$CH(CH_3)CH_2$— | | $n_D^{25}$ = 1.4533 |
| 41 | n-nonyl | O | $(CH_2)_4$ | —$(CH_2)_6$— | | 132–134/0.3 |
| 42 | 5-ethylhept-2-yl | O | $(CH_2)_4$ | —$CH_2$—$CH(CH_3)O$—$CH(CH_3)CH_2$— | | $n_D^{22}$ = 1.4534 |
| 43 | 5-ethylhept-2-yl | O | $(CH_2)_6$ | —$CH_2$—$CH(CH_3)O$—$CH(CH_3)CH_2$— | | $n_D^{22}$ = 1.4577 |
| 44 | 5-ethylhept-2-yl | O | $(CH_2)_4$ | —$(CH_2)_2N(CH_3)(CH_2)_2$— | | 130–134/0.3 |
| 45 | 3,5,5-trimethylhex-1-yl | O | $(CH_2)_4$ | —$(CH_2)_2N(CH_3)(CH_2)_2$— | | 137–140/0.4 |
| 46 | 3,5,5-trimethylhex-1-yl | O | $(CH_2)_4$ | —$(CH_2)_2N(CH_3)(CH_2)_2$— | | 145/0.2 |
| 47 | 3,5,5-trimethylhex-1-yl | O | $(CH_2)_4$ | ethyl | n-butyl | $n_D^{22}$ = 1.4432 |
| 48 | 3,5,5-trimethylhex-1-yl | O | $(CH_2)_4$ | —$CH_2$—$CH(CH_3)O$—$CH(CH_3)CH_2$— | | $n_D^{22}$ = 1.4530 |
| 49 | 3,5,5-trimethylhex-1-yl | O | $(CH_2)_4$ | —$CH_2$—$CH(CH_3)O$—$CH(CH_3)CH_2$— | | $n_D^{22}$ = 1.4545 |
| 50 | 3,5,5-trimethylhex-1-yl | O | $(CH_2)_4$ | —$(CH_2)_6$— | | $n_D^{22}$ = 1.4635 |
| 51 | 2-ethylhex-1-yl | O | $(CH_2)_4$ | —$(CH_2)_6$— | | 128–131/0.3 |
| 52 | 2-ethylhex-1-yl | O | $(CH_2)_4$ | —$(CH_2)_5$— | | 125–129/0.3 |
| 53 | 2-ethylhex-1-yl | O | $(CH_2)_4$ | —$(CH_2)_3CH(CH_3)$— | | 134–136/0.4 |
| 54 | 2-ethylhex-1-yl | O | $(CH_2)_4$ | —$(CH_2)_3CH(CH_3)CH_2$— | | 127–130/0.3 |
| 55 | 2-ethylhex-1-yl | O | $(CH_2)_4$ | —$(CH_2)_2CH(CH_3)(CH_2)_2$ | | 133–134/0.4 |
| 56 | 2-ethylhex-1-yl | O | $(CH_2)_4$ | —$(CH_2)_2CH[C(CH_3)_3](CH_2)_2$— | | 145–148/0.3 |
| 57 | 2-ethylhex-1-yl | O | $(CH_2)_3$ | —$CH_2CH(CH_3)OCH(CH_3)CH_2$— | | $n_D^{22}$ = 1.4507 |
| 58 | 2-ethylhex-1-yl | O | $(CH_2)_4$ | —$CH_2CH(CH_3)OCH(CH_3)CH_2$— | | $n_D^{22}$ = 1.4525 |
| 59 | 2-ethylhex-1-yl | O | $(CH_2)_5$ | —$CH_2CH(CH_3)OCH(CH_3)CH_2$— | | $n_D^{22}$ = 1.4528 |
| 60 | 2-ethylhex-1-yl | O | $(CH_2)_6$ | —$CH_2CH(CH_3)OCH(CH_3)CH_2$— | | $n_D^{22}$ = 1.4549 |
| 61 | 2-ethylhex-1-yl | O | $(CH_2)_4$ | —$(CH_2)_2N(CH_3)(CH_2)_2$— | | 133–135/0.4 |
| 62 | 2-ethylhex-1-yl | O | $(CH_2)_6$ | —$(CH_2)_2N(CH_3)(CH_2)_2$— | | 152–154/0.4 |
| 63 | 5-methyl-2-isopropylhex-1-yl | O | $(CH_2)_4$ | —$(CH_2)_2N(CH_3)(CH_2)_2$— | | 140–142/0.4 |
| 64 | 5-methyl-2-isopropylhex-1-yl | O | $(CH_2)_4$ | —$CH_2CH(CH_3)OCH(CH_3)CH_2$— | | $n_D^{25}$ = 1.4540 |
| 65 | 3,7-dimethyloct-1-yl | O | $(CH_2)_4$ | —$CH_2CH(CH_3)OCH(CH_3)CH_2$— | | $n_D^{25}$ = 1.4545 |
| 66 | 3,7-dimethyloct-1-yl | O | $(CH_2)_6$ | —$CH_2CH(CH_3)OCH(CH_3)CH_2$— | | $n_D^{25}$ = 1.4565 |
| 67 | 3,7-dimethyloct-1-yl | O | $(CH_2)_4$ | —$(CH_2)_2M(CH_3)(CH_2)_2$— | | 145–148/0.4 |
| 68 | 3,7-dimethyloct-1-yl | O | $(CH_2)_6$ | —$(CH_2)_2M(CH_3)(CH_2)_2$— | | 146–150/0.3 |
| 69 | 3,7-dimethyloct-1-yl | O | $(CH_2)_4$ | methyl | cyclohexyl | $n_D^{22}$ = 1.4642 |
| 70 | 3,7-dimethyloct-1-yl | S | $(CH_2)_4$ | —$CH_2CH(CH_3OCH(CH_3)CH_2$— | | 167–169/0.4 |
| 71 | n-decyl | S | $(CH_2)_3$ | —$CH_2CH(CH_3OCH(CH_3)CH_2$— | | $n_D^{23}$ = 1.4781 |
| 72 | 2-(n-butyl)-oct-1-yl | O | $(CH_2)_3$ | —$CH_2CH(CH_3OCH(CH_3)CH_2$— | | $n_D^{23}$ = 1.4555 |
| 73 | 2-(n-butyl)-oct-1-yl | O | $(CH_2)_4$ | —$CH_2CH(CH_3OCH(CH_3)CH_2$— | | $n_D^{25}$ = 1.4550 |
| 74 | 2-(n-butyl)-oct-1-yl | O | $(CH_2)_5$ | —$CH_2CH(CH_3OCH(CH_3)CH_2$— | | $n_D^{22}$ = 1.4569 |
| 75 | 2-(n-butyl)-oct-1-yl | O | $(CH_2)_6$ | —$CH_2CH(CH_3OCH(CH_3)CH_2$— | | $n_D^{22}$ = 1.4570 |
| 76 | 2-(n-butyl)-oct-1-yl | O | $(CH_2)_4$ | —$(CH_2)_5$— | | $n_D^{22}$ = 1.4607 |

-continued

| Example No. | A | X | B | R¹ | R² | Refractive index or bp. [°C./mbar] |
|---|---|---|---|---|---|---|
| 77 | 2-(n-butyl)-oct-1-yl | O | (CH$_2$)$_4$ | —(CH$_2$)$_2$N(CH$_3$)(CH$_2$)$_2$— | | 150–152/0.3 |
| 78 | 3-methylhept-1-yl | O | (CH$_2$)$_4$ | —(CH$_2$)$_2$N(CH$_3$)(CH$_2$)$_2$— | | 128–130/0.2 |
| 79 | 3-methylhept-1-yl | O | (CH$_2$)$_4$ | —CH$_2$—CH(CH$_3$)OCH(CH$_3$)CH$_2$— | | n$_D^{22}$ = 1.4538 |
| 80 | n-undecyl | O | (CH$_2$)$_4$ | —CH$_2$—CH(CH$_3$)OCH(CH$_3$)CH$_2$— | | n$_D^{22}$ = 1.4558 |
| 81 | n-undecyl | O | (CH$_2$)$_4$ | —(CH$_2$)$_2$N(CH$_3$)(CH$_2$)$_2$— | | 168/0.4 |
| 82 | 2-(n-hexyl)-dec-1-yl | O | (CH$_2$)$_4$ | —(CH$_2$)$_2$N(CH$_3$)(CH$_2$)$_2$— | | 190/0.3 |
| 83 | 2-(n-hexyl)-dec-1-yl | O | (CH$_2$)$_4$ | —CH$_2$—CH(CH$_3$)OCH(CH$_3$)CH$_2$— | | n$_D^{26}$ = 1.4562 |
| 84 | 3,7,11-trimethyldodec-1-yl | O | (CH$_2$)$_4$ | —CH$_2$—CH(CH$_3$)OCH(CH$_3$)CH$_2$— | | n$_D^{26}$ = 1.4557 |
| 85 | 2-(n-hexyl)-dec-1-yl | O | (CH$_2$)$_4$ | —CH$_2$—CH(CH$_3$)OCH(CH$_3$)CH$_2$— | | 200–202/0.6 |
| 86 | 2-(1,3,3-trimethylbutyl-1)-5,7,7-trimethyloct-1-yl | O | (CH$_2$)$_4$ | —CH$_2$—CH(CH$_3$)OCH(CH$_3$)CH$_2$— | | n$_D^{26}$ = 1.4581 |
| 87 | 8-chlorooct-1-yl | O | (CH$_2$)$_4$ | —CH$_2$—CH(CH$_3$)OCH(CH$_3$)CH$_2$— | | 133–135/0.3 |
| 88 | CF$_3$CF$_2$CF$_2$CH$_2$— | O | (CH$_2$)$_4$ | —CH$_2$—CH(CH$_3$)OCH(CH$_3$)CH$_2$— | | |
| 89 | CF$_3$CF$_2$CF$_2$CH$_2$— | O | (CH$_2$)$_6$ | —CH$_2$—CH(CH$_3$)OCH(CH$_3$)CH$_2$— | | |
| 90 | CF$_3$—(CF$_2$)$_9$—CH$_2$—CH$_2$ | O | (CH$_2$)$_4$ | —CH$_2$—CH(CH$_3$)OCH(CH$_3$)CH$_2$— | | n$_D^{25}$ = 1.4335 |
| 91 | cyclopentyl | O | (CH$_2$)$_4$ | —CH$_2$—CH(CH$_3$)OCH(CH$_3$)CH$_2$— | | n$_D^{22}$ = 1.4655 |
| 92 | cyclohexyl | O | (CH$_2$)$_4$ | —CH$_2$—CH(CH$_3$)OCH(CH$_3$)CH$_2$— | | n$_D^{22}$ = 1.4639 |
| 93 | cyclohexyl | O | (CH$_2$)$_6$ | —CH$_2$—CH(CH$_3$)OCH(CH$_3$)CH$_2$— | | n$_D^{22}$ = 1.4643 |
| 94 | cyclohexylmethyl | O | (CH$_2$)$_4$ | —CH$_2$—CH(CH$_3$)OCH(CH$_3$)CH$_2$— | | 136–140/0.4 |
| 95 | (2-isopropyl-5-methyl)-cyclohex-1-yl | O | (CH$_2$)$_4$ | —CH$_2$—CH(CH$_3$)OCH(CH$_3$)CH$_2$— | | n$_D^{21}$ = 1.4685 |
| 96 | (2-isopropyl-5-methyl)-cyclohex-1-yl | O | (CH$_2$)$_6$ | —CH$_2$—CH(CH$_3$)OCH(CH$_3$)CH$_2$— | | n$_D^{22}$ = 1.4690 |
| 97 | (2-isopropyl-5-methyl)-cyclohex-1-yl | O | (CH$_2$)$_4$ | —(CH$_2$)$_2$N(CH$_3$)(CH$_2$)$_2$— | | 135–137/0.3 |
| 98 | (4-tert.-butyl)-cyclohexyl | O | (CH$_2$)$_4$ | —CH$_2$—CH(CH$_3$)OCH(CH$_3$)CH$_2$— | | n$_D^{22}$ = 1.4716 |
| 99 | (4-tert.-butyl)-cyclohexyl | O | (CH$_2$)$_6$ | —CH$_2$—CH(CH$_3$)OCH(CH$_3$)CH$_2$— | | n$_D^{22}$ = 1.4710 |
| 100 | (4-tert.-butyl)-cyclohexyl | O | (CH$_2$)$_4$ | —(CH$_2$)$_2$N(CH$_3$)(CH$_2$)$_2$— | | 154–156/0.4 |
| 101 | (4-tert.-amyl)-cyclohexyl | O | (CH$_2$)$_4$ | —CH$_2$—CH(CH$_3$)OCH(CH$_3$)CH$_2$— | | n$_D^{22}$ = 1.4751 |
| 102 | (4-tert.-amyl)-cyclohexyl | O | (CH$_2$)$_6$ | —CH$_2$—CH(CH$_3$)OCH(CH$_3$)CH$_2$— | | n$_D^{22}$ = 1.4745 |
| 103 | (4-tert.-amyl)-cyclohexyl | O | (CH$_2$)$_4$ | —(CH$_2$)$_5$ | | |
| 104 | (4-tert.-amyl)-cyclohexyl | O | (CH$_2$)$_6$ | —(CH$_2$)$_5$ | | |
| 105 | (4-tert.-amyl)-cyclohexyl | O | (CH$_2$)$_4$ | —(CH$_2$)$_2$N(CH$_3$)(CH$_2$)$_2$— | | 168–170/0.4 |
| 106 | (4-tert.-amyl)-cyclohexyl | O | (CH$_2$)$_6$ | —(CH$_2$)$_2$N(CH$_3$)(CH$_2$)$_2$— | | 183–186/0.3 |
| 107 | (4-tert.-amyl)-cyclohexyl | O | (CH$_2$)$_4$ | —(CH$_2$)$_3$CH(CH$_3$)CH$_2$ | | 183–185/0.3 |
| 108 | 3,5,5-dimethylcyclohexyl | O | (CH$_2$)$_4$ | —CH$_2$—CH(CH$_3$)OCH(CH$_3$)CH$_2$— | | n$_D^{22}$ = 1.4672 |
| 109 | 3,5,5-dimethylcyclohexyl | O | (CH$_2$)$_5$ | —CH$_2$—CH(CH$_3$)OCH(CH$_3$)CH$_2$— | | |
| 110 | 3,5,5-dimethylcyclohexyl | O | (CH$_2$)$_6$ | —CH$_2$—CH(CH$_3$)OCH(CH$_3$)CH$_2$— | | |
| 111 | 3,5,5-dimethylcyclohexyl | O | —CH$_2$—CH(CH$_3$)CH$_2$ | —CH$_2$—CH(CH$_3$)OCH(CH$_3$)CH$_2$— | | n$_D^{22}$ = 1.4672 |
| 112 | 3,5,5-dimethylcyclohexyl | O | (CH$_2$)$_4$ | —(CH$_2$)$_2$N(CH$_3$)(CH$_2$)$_2$— | | 140–143/0.4 |
| 113 | 3,5,5-dimethylcyclohexyl | O | (CH$_2$)$_4$ | —(CH$_2$)$_5$ | | |
| 114 | 3,5,5-dimethylcyclohexyl | O | (CH$_2$)$_4$ | —(CH$_2$)$_3$CH(CH$_3$)CH$_2$— | | |
| 115 | 2-(cyclohexyl)-prop-1-yl | O | (CH$_2$)$_4$ | —(CH$_2$)$_2$N(CH$_3$)(CH$_2$)$_2$— | | 150–152/0.4 |
| 116 | 2-(cyclohexyl)-prop-1-yl | O | (CH$_2$)$_4$ | —CH$_2$—CH(CH$_3$)OCH(CH$_3$)CH$_2$— | | n$_D^{22}$ = 1.4731 |
| 117 | 2-(cyclohexyl)-prop-1-yl | O | (CH$_2$)$_6$ | —CH$_2$—CH(CH$_3$)OCH(CH$_3$)CH$_2$— | | 140–142/0.4 |
| 118 | 2-(cyclohexyl)-prop-1-yl | O | —CH$_2$—CH(CH$_3$)CH$_2$ | —CH$_2$—CH(CH$_3$)OCH(CH$_3$)CH$_2$— | | 134–136/0.3 |
| 119 | 2-(cyclohexyl)-prop-1-yl | O | (CH$_2$)$_4$ | (CH$_2$)$_5$ | | |
| 120 | 2-(cyclohexyl)-prop-1-yl | O | (CH$_2$)$_4$ | —(CH$_2$)$_3$CH(CH$_3$)CH$_2$— | | |
| 121 | 4-(cyclohexyl)-cyclohexyl | O | (CH$_2$)$_4$ | —CH$_2$—CH(CH$_3$)OCH(CH$_3$)CH$_2$— | | n$_D^{22}$ = 1.4871 |
| 122 | 4-(cyclohexyl)-cyclohexyl | O | (CH$_2$)$_6$ | —CH$_2$—CH(CH$_3$)OCH(CH$_3$)CH$_2$— | | |
| 123 | cycloheptyl | O | (CH$_2$)$_4$ | —CH$_2$—CH(CH$_3$)OCH(CH$_3$)CH$_2$— | | n$_D^{22}$ = 1.4740 |
| 124 | 1-norbonyl | O | (CH$_2$)$_4$ | —CH$_2$—CH(CH$_3$)OCH(CH$_3$)CH$_2$— | | n$_D^{22}$ = 1.4784 |
| 125 | 1-norbonyl | O | (CH$_2$)$_6$ | —CH$_2$—CH(CH$_3$)OCH(CH$_3$)CH$_2$— | | n$_D^{22}$ = 1.4780 |
| 126 | 1-norbonyl | O | (CH$_2$)$_4$ | —(CH$_2$)$_2$N(CH$_3$)(CH$_2$)$_2$— | | 122–124/0.3 |
| 127 | 1-norbonyl | O | (CH$_2$)$_6$ | —(CH$_2$)$_2$N(CH$_3$)(CH$_2$)$_2$— | | 140–142/0.3 |
| 128 | 3,3-dimethyl-2,4-endomethylene-cyclohexylmethyl | O | (CH$_2$)$_4$ | —(CH$_2$)$_2$N(CH$_3$)(CH$_2$)$_2$— | | 168–170/0.3 |
| 129 | 3,3-dimethyl-2,4-endomethylene-cyclohexylmethyl | O | (CH$_2$)$_4$ | —CH$_2$—CH(CH$_3$)OCH(CH$_3$)CH$_2$— | | n$_D^{22}$ = 1.4811 |
| 130 | 3,3-dimethyl-2,4-endomethylene-cyclohexylmethyl | O | (CH$_2$)$_6$ | —CH$_2$—CH(CH$_3$)OCH(CH$_3$)CH$_2$— | | 159–160/0.3 |
| 131 | 3,3-dimethyl-2,4-endomethylene-cyclohexylmethyl | O | —CH$_2$—CH(CH$_3$)CH$_2$— | —CH$_2$—CH(CH$_3$)OCH(CH$_3$)CH$_2$— | | 151–153/0.3 |
| 132 | 1-decatyl | O | (CH$_2$)$_4$ | —CH$_2$—CH(CH$_3$)OCH(CH$_3$)CH$_2$— | | |
| 133 | 2-decalyl | O | (CH$_2$)$_4$ | —CH$_2$—CH(CH$_3$)OCH(CH$_3$)CH$_2$— | | |
| 134 | 2-(2,2-dimethyl-3,6-endo-methylencyclohexyl)-eth-1-yl | O | (CH$_2$)$_4$ | —CH$_2$—CH(CH$_3$)OCH(CH$_3$)CH$_2$— | | |
| 135 | 2-(2,2-dimethyl-3,6-endo-methylencyclohexyl)-ethyl-1 | O | (CH$_2$)$_6$ | —CH$_2$—CH(CH$_3$)OCH(CH$_3$)CH$_2$— | | |
| 136 | 2-(2,2,3-trimethylcyclopent-3-en-1-yl)-ethyl-1 | O | (CH$_2$)$_4$ | —CH$_2$—CH(CH$_3$)OCH(CH$_3$)CH$_2$— | | |
| 137 | 2-(2,2,3-trimethylcyclopent-3-en-1-yl)-eth-1yl | O | (CH$_2$)$_6$ | —CH$_2$—CH(CH$_3$)OCH(CH$_3$)CH$_2$— | | |
| 138 | isobornyl | O | (CH$_2$)$_4$ | —CH$_2$—CH(CH$_3$)OCH(CH$_3$)CH$_2$— | | |
| 139 | allyl | O | (CH$_2$)$_6$ | —CH$_2$—CH(CH$_3$)OCH(CH$_3$)CH$_2$— | | 125–118/0.3 |
| 140 | methallyl | O | (CH$_2$)$_6$ | —CH$_2$—CH(CH$_3$)OCH(CH$_3$)CH$_2$— | | 120–121/0.3 |
| 141 | 2,3,3-trichloroallyl | O | (CH$_2$)$_4$ | —CH$_2$—CH(CH$_3$)OCH(CH$_3$)CH$_2$— | | n$_D^{22}$ = 1.4940 |
| 142 | 2,3,3-trichloroallyl | O | (CH$_2$)$_6$ | —CH$_2$—CH(CH$_3$)OCH(CH$_3$)CH$_2$— | | n$_D^{22}$ = 1.4875 |
| 143 | benzyl | O | (CH$_2$)$_2$ | —CH$_2$—CH(CH$_3$)OCH(CH$_3$)CH$_2$— | | 135–138/0.2 |
| 144 | benzyl | O | —CH$_2$—CH(CH$_3$)CH$_2$— | —CH$_2$—CH(CH$_3$)OCH(CH$_3$)CH$_2$— | | 138–143/0.4 |

-continued

| Example No. | A | X | B | R¹ | R² | Refractive index or bp. [°C./mbar] |
|---|---|---|---|---|---|---|
| 145 | 4-methylbenzyl | O | (CH₂)₂ | —(CH₂)₄— | | 90–98/0.1 |
| 146 | 4-chlorobenzyl | O | (CH₂)₂ | —(CH₂)₄— | | 128–131/0.1 |
| 147 | 2,6-dichlorobenzyl | O | (CH₂)₂ | —CH₂—CH(CH₃)OCH(CH₃)CH₂— | | 158–163/0.4 |
| 148 | 2,6-dichlorohydrochloride | O | (CH₂)₂ | —CH₂—CH(CH₃)OCH(CH₃)CH₂— | | 202–204° C. |
| 149 | 2,6-dichlorobenzyl | O | (CH₂)₂ | —CH₂—CH(CH₃)OCH(CH₃)CH₂— | | 155–158/0.5 |
| 150 | 4-tert.-butylbenzyl | O | (CH₂)₂ | —CH₂—CH(CH₃)OCH(CH₃)CH₂— | | 156/0.1 |
| 151 | 4-tert.-butylbenzyl | O | (CH₂)₂ | —(CH₂)₅— | | 126–130/0.1 |
| 152 | 4-tert.-butylbenzyl | O | (CH₂)₂ | —(CH₂)₃CH(CH₃)CH₂— | | 140–141/0.1 |
| 153 | 3-phenyl-prop-1-yl | O | (CH₂)₄ | —CH₂—CH(CH₃)OCH(CH₃)CH₂— | | $n_D^{22} = 1.4978$ |
| 154 | 3-phenyl-prop-1-yl | O | (CH₂)₆ | —CH₂—CH(CH₃)OCH(CH₃)CH₂— | | $n_D^{22} = 1.4925$ |
| 155 | 3-phenyl-prop-1-yl | O | (CH₂)₅ | —CH₂—CH(CH₃)OCH(CH₃)CH₂— | | $n_D^{21} = 1.4931$ |
| 156 | 3-phenyl-2-methylprop-1-yl | O | (CH₂)₄ | —CH₂—CH(CH₃)OCH(CH₃)CH₂— | | $n_D^{22} = 1.4953$ |
| 157 | 3-phenyl-2-methylprop-1-yl | O | (CH₂)₆ | —CH₂—CH(CH₃)OCH(CH₃)CH₂— | | $n_D^{22} = 1.4930$ |
| 158 | 3-(4-isopropylphenyl)-2-methyl-prop-1-yl | O | (CH₂)₄ | —CH₂—CH(CH₃)OCH(CH₃)CH₂— | | |
| 159 | 3-(4-isopropylphenyl)-2-methyl-prop-1-yl | O | (CH₂)₆ | —CH₂—CH(CH₃)OCH(CH₃)CH₂— | | $n_D^{22} = 1.4899$ |
| 160 | 3-(4-tert.-butylphenyl)-2-methylprop-1-yl | O | (CH₂)₄ | n-C₃H₇ | | 170–172/0.2 |
| 161 | 3-(4-tert.-butylphenyl)-2-methylprop-1-yl | O | (CH₂)₆ | C₂H₅ | | 185–188/032 |
| 162 | 3-(4-tert.-butylphenyl)-2-methylprop-1-yl | O | (CH₂)₄ | —CH₂—CH(CH₃)OCH(CH₃)CH₂— | | 179–180/0.2 |
| 163 | 3-(4-tert.-butylphenyl)-2-methylprop-1-yl | O | (CH₂)₅ | —CH₂—CH(CH₃)OCH(CH₃)CH₂— | | $n_D^{22} = 1.4922$ |
| 164 | 3-(4-tert.-butylphenyl)-2-methylprop-1-yl | O | (CH₂)₆ | —CH₂—CH(CH₃)OCH(CH₃)CH₂— | | $n_D^{22} = 1.4915$ |
| 165 | 3-(4-tert.-butylphenyl)-2-methylprop-1-yl | O | (CH₂)₈ | —CH₂—CH(CH₃)OCH(CH₃)CH₂— | | $n_D^{22} = 1.4909$ |
| 166 | 3-(4-tert.-butylphenyl)-2-methylprop-1-yl | O | (CH₂)₄ | (CH₂)₅ | | |
| 167 | 3-(4-tert.-butylphenyl)-2-methylprop-1-yl | O | (CH₂)₄ | —CH₂—CH(CH₃)OCH(CH₃)CH₂— | | |
| 168 | 3-(4-tert.-butylphenyl)-2-methylprop-1-yl | O | (CH₂)₄ | —CH₂—CH(CH₃)CH₂CH(CH₃)CH₂ | | |
| 169 | 5-phenyl-2,4-dimethyl-pent-1-yl | O | (CH₂)₄ | —CH₂—CH(CH₃)OCH(CH₃)CH₂— | | $n_D^{22} = 1.4931$ |
| 170 | 5-phenyl-2,4-dimethyl-pent-1-yl | O | (CH₂)₆ | —CH₂—CH(CH₃)OCH(CH₃)CH₂— | | $n_D^{22} = 1.4920$ |

In general terms, the novel compounds are very effective against a broad spectrum of phytopathogenic fungi, in particular those from the class consisting of the Ascomycetes and Basidiomycetes. Some of them have a systemic action and can be used as foliar and soil fungicides.

The fungicidal compounds are of particular interest for controlling a large number of fungi on various crops or their seeds, in particular wheat, rye, barley, oats, rice, corn, cotton, soybean, coffee, sugar cane, fruit and ornamentals in horticulture, in viticulture, and for vegetables, such as cucumbers, beans and Cucurbitaceae.

The novel compounds are particularly useful for controlling the following plant diseases:
*Erysiphe graminis* in cereals,
*Erysiphe cichoracearum* and *Sphaerotheca fuliginea* in Cucurbitaceae,
*Podosphaera leucotricha* in apples,
*Uncinula necator* in vines,
Puccinia species in cereals,
*Rhizoctonia solani* in cotton,
Ustilago species in cereals and sugar cane,
*Venturia inaequal* is (scab) in apples,
*Septoria nodorum* in wheat,
*Pyrenophora teres* in barley,
*Botrytis cinerea* (gray mold) in strawberries and vines,
*Cercospora musae* in bananas,
*Pseudocercosporella herpotrichoides* in wheat and barley,
*Pyricularia oryzae* in rice,
*Hemileia vastatrix* in coffee,
*Alternaria solani* in potatoes and tomatoes,
*Plasmopara viticola* in vines, and
Fusarium and Verticillium species in various plants.

The compounds are applied by spraying or dusting plants with the active ingredients, or treating the seeds of the plants with the active ingredients. They are applied before or after infection of the plants or seeds with the fungi.

The novel substances can be converted to the conventional formulations, such as solutions, emulsions, suspensions, dusts, powders, pastes and granules. The forms for use depend entirely on the purposes for which they are intended; they should at all events ensure a fine and uniform distribution of the active substance. The formulations are produced in a known manner, for example by extending the active ingredient with solvents and/or carriers, with or without the use of emulsifiers and dispersants; if water is used as a diluent, it is also possible to employ other, organic solvents as auxiliary solvents. Suitable assistants for this purpose are essentially solvents, such as aromatics (eg. xylene or benzene), chlorinated aromatics (eg. chlorobenzenes), paraffins (eg. oil fractions), alcohols (eg. methanol or butanol), ketones (eg. cyclohexanone), amines (eg. ethanolamine or dimethylformamide) and water; carriers, such as ground natural minerals (kaolins, aluminas, talc or chalk) and ground synthetic minerals (eg. highly disperse silica or silicates); emulsifiers, such as nonionic and anionic emulsifiers (eg. polyoxyethylene fatty alcohol ethers, alkylsulfonates and arylsulfonates) and dispersants, such as lignin, sulfite waste liquors and methylcellulose.

The fungicides generally contain from 0.1 to 95, preferably from 0.5 to 90, % by weight of active ingredient.

The application rates are from 0.02 to 3 kg or more of active ingredient per ha, depending on the type of effect desired. The novel compounds may also be employed in material protection, inter alia for controlling wood-destroying fungi, such as Coniophora puteana and Polystictus versicolor. The novel active ingredients can also be used as fungicidal components of oily wood preservatives for protecting wood against wood-discoloring fungi. They are used by treating, for example impregnating or painting, the wood with these agents.

The agents and the ready-to-use formulations prepared from them, such as solutions, emulsions, suspensions, powders, dusts, pastes or granules, are applied in a conventional manner, for example by spraying, misting, dusting, scattering, dressing or watering.

Examples of such formulations are:

I. 90 parts by weight of compound No. 3 are mixed with 10 parts by weight of N-methyl-alpha-pyrrolidone to give a solution which is suitable for application in the form of very small drops.

II. 20 parts by weight of compound No. 23 are dissolved in a mixture which consists of 80 parts by weight of xylene, 10 parts by weight of the adduct of from 8 to 10 moles of ethylene oxide with 1 mole of oleic acid N-monoethanolamide, 5 parts by weight of calcium dodecylbenzenesulfonate and 5 parts by weight of the adduct of 40 moles of ethylene oxide with 1 mole of castor oil. By pouring the solution into water and dispersing it finely, an aqueous dispersion is obtained.

III. 20 parts by weight of compound No. 24 are dissolved in a mixture which consists of 40 parts by weight of cyclohexanone, 30 parts by weight of isobutanol and 20 parts by weight of the adduct of 40 moles of ethylene oxide with 1 mole of castor oil. By pouring the solution into water and dispersing it finely, an aqueous dispersion is obtained.

IV. 20 parts by weight of compound No. 26 are dissolved in a mixture which consists of 25 parts by weight of cyclohexanol, 65 parts by weight of a mineral oil fraction having a boiling point of from 210° to 280° C. and 10 parts by weight of the adduct of 40 moles of ethylene oxide with 1 mole of castor oil. By pouring the solution into water and dispersing it finely, an aqueous dispersion is obtained.

V. 80 parts by weight of compound No. 27 are mixed thoroughly with 3 parts by weight of sodium diisobutylnaphthalene-alpha-sulfonate, 10 parts by weight of the sodium salt of a ligninsulfonic acid obtained from a sulfite waste liquor, and 7 parts by weight of powdered silica gel, and the mixture is milled in a hammer mill. By finely dispersing the mixture in water, a spray liquor is obtained.

VI. 3 parts by weight of compound No. 42 are mixed intimately with 97 parts by weight of finely divided kaolin to give a dusting agent which contains 3% by weight of the active ingredient.

VII. 30 parts by weight of compound No. 57 are mixed intimately with a mixture of 92 parts by weight of powdered silica gel and 8 parts by weight of paraffin oil, which has been sprayed onto the surface of this silica gel. This gives a formulation of the active ingredient which possesses good adhesive power.

VIII. 40 parts by weight of compound No. 59 are mixed thoroughly with 10 parts of the sodium salt of a phenolsulfonic acid/urea/formaldehyde condensate, 2 parts of silica gel and 48 parts of water to give a stable aqueous dispersion. By dilution with water, an aqueous dispersion is obtained.

IX. 20 parts of compound No. 74 are mixed thoroughly with 2 parts of calcium dodecylbenzenesulfonate, 8 parts of a fatty alcohol polyglycol ether, 2 parts of the sodium salt of a phenolsulfonic acid/urea/formaldehyde condensate and 68 parts of a paraffinic mineral oil. A stable oily dispersion is obtained.

In these application forms, the agents according to the invention may also be present together with other active ingredients, for example herbicides, insecticides, growth regulators and fungicides, or may furthermore be mixed with fertilizers and applied together with these. Mixing with fungicides frequently results in a greater fungicidal action spectrum.

The following list of fungicides with which the novel compounds may be combined is intended to illustrate possible combinations but not to impose any restrictions.

Examples of fungicides which may be combined with the novel compounds are:
sulfur,
dithiocarbamates and their derivatives, such as
ferric dimethyldithiocarbamate,
zinc dimethyldithiocarbamate,
zinc ethylenebisdithiocarbamate,
manganese ethylenebisdithiocarbamate,
manganese zinc ethylenediaminebisdithiocarbamate,
tetramethylthiuram disulfides,
ammonia complex of zinc N,N'-ethylenebisdithiocarbamate,
ammonia complex of zinc N,N'-propylenebisdithiocarbamate,
zinc N,N'-propylenebisdithiocarbamate and
N,N'-polypropylenebis(thiocarbamyl)disulfide;
nitro derivatives, such as
dinitro(1-methylheptyl)-phenyl crotonate,
2-sec-butyl-4,6-dinitrophenyl 3,3-dimethylacrylate,
2-sec-butyl-4,6-dinitrophenyl isopropylcarbonate and
diisopropyl 5-nitroisophthalate;
heterocyclic substances, such as
2-heptadecylimidazol-2-yl acetate,
2,4-dichloro-6-(o-chloroanilino)-s-triazine,
0,0-diethyl phthalimidophosphonothioate,
5-amino-1-[bis-(dimethylamino)-phosphinyl]-3-phenyl-1,2,4-triazole,
2,3-dicyano-1,4-dithiaanthraquinone,
2-thio-1,3-dithio[4,5-b]quinoxaline,
methyl 1-(butylcarbamyl)-2-benzimidazolecarbamate,
2-methoxycarbonylaminobenzimidazole,
2-(fur-2-yl)-benzimidazole,
2-(thiazol-4-yl)benzimidazole,
N-(1,1,2,2-tetrachloroethylthio)-tetrahydrophthalimide,
N-trichloromethylthiotetrahydrophthalimide,
N-trichloromethylthiophthalimide,
N-dichlorofluoromethylthio-N',N'-dimethyl-N-phenylsulfuric acid diamide,
5-ethoxy-3-trichloromethyl-1,2,3-thiadiazole,
2-thiocyanatomethylthiobenzothiazole,
1,4-dichloro-2,5-dimethoxybenzene,
4-(2-chlorophenylhydrazono)-3-methyl-5-isoxazolone,
2-thiopyridine 1-oxide,
8-hydroxyquinoline and its copper salt,
2,3-dihydro-5-carboxanilido-6-methyl-1,4-oxathiin,
2,3-dihydro-5-carboxanilido-6-methyl-1,4-oxathiin 4,4-dioxide,
2-methyl-5,6-dihydro-4H-pyran-3-carboxanilide, 2-methylfuran-3-carboxanilide,
2,5-dimethylfuran-3-carboxanilide,
2,4,5-trimethylfuran-3-carboxanilide,
2,5-dimethyl-N-cyclohexylfuran-3-carboxamide,
N-cyclohexyl-N-methoxy-2,5-dimethylfuran-3-carboxamide,
2-methylbenzanilide,
2-iodobenzanilide,
N-formyl-N-morpholine-2,2,2-trichloroethylacetal,
piperazine-1,4-diylbis-(1-(2,2,2-trichloroethyl)-formamide),
1-(3,4-dichloroanilino)-1-formylamino-2,2,2-trichloroethane,
2,6-dimethyl-N-tridecylmorpholine and its salts,
2,6-dimethyl-N-cyclododecylmorpholine and its salts,
N-[3-(p-tert.-butylphenyl)-2-methylpropyl]-cis-2,6-dimethylmorpholine,
N-[3-(p-tert.-butylphenyl)-2-methylpropyl]-piperidine,
1-[2-(2,4-dichlorophenyl)-4-ethyl-1,3-dioxolan-2-ylethyl]-1H-1,2,4-triazole,
1-[2-(2,4-dichlorophenyl)-4-n-propyl-1,3-dioxolan-2-ylethyl]-1H-1,2,4-triazole,
N-(n-propyl)-N-(2,4,6-trichlorophenoxyethyl)-N'-imidazolylurea,
1-(4-chlorophenoxy)-3,3-dimethyl-1-(1H-1,2,4-triazol-1-yl)-butan-2-one,
1-(4-chlorophenoxy)-3,3-dimethyl-1-(1H-1,2,4-triazol-1-yl)-butan-2-ol,
α-(2-chlorophenyl)-α-(4-chlorophenyl)-5-pyrimidinemethanol,
5-butyl-2-dimethylamino-4-hydroxy-6-methylpyrimidine,
bis-(p-chlorophenyl)-3-pyridinemethanol,
1,2-bis-(3-ethoxycarbonyl-2-thioureido)-benzene,
1,2-bis-(3-methoxycarbonyl-2-thioureido)-benzene,
and various fungicides, such as
dodecylguanidine acetate,
3-[3-(3,5-dimethyl-2-oxycyclohexyl)-2-hydroxyethyl]-glutaramide,
hexachlorobenzene,
DL-methyl-N-(2,6-dimethylphenyl)-N-fur-2-yl alanate,
methyl DL-N-(2,6-dimethylphenyl)-N-(2'-methoxyacetyl)-alanate,
N-(2,6-dimethylphenyl)-N-chloroacetyl-DL-2-aminobutyrolactone,
methyl DL-N-(2,6-dimethylphenyl)-N-(phenylacetyl)-alanate,
5-methyl-5-vinyl-3-(3,5-dichlorophenyl)-2,4-dioxo-1,3-oxazolidine,
3-[3,5-dichlorophenyl]-5-methyl-5-methoxymethyl-1,3-oxazolidine-2,4-dione,
3-(3,5-dichlorophenyl)-1-isopropylcarbamylhydantoin,
N-(3,5-dichlorophenyl)-1,2-dimethylcyclopropane-1,2-dicarboximide,
2-cyano-[N-(ethylaminocarbonyl)-2-methoximino]-acetamide,
1-[2-(2,4-dichlorophenyl)-pentyl]-1H-1,2,4-triazole and
2,4-difluoro-α-(1H-1,2,4-triazol-1-ylmethyl)-benzhydryl alcohol.

For the tests below, the known active ingredients N-tridecyl-2,6-dimethylmorpholine (A) and its acetate (B) were used as comparisons.

USE EXAMPLE 1

Action on powdery mildew of wheat

Leaves of pot-grown wheat seedlings of the Frühgold variety were sprayed with aqueous spray liquor containing (dry basis) 80% of active ingredient and 20% of emulsifier, and, 24 hours after the spray coating had dried on, the leaves were dusted with oidia (spores) of powdery mildew of wheat (*Erysiphe graminis* var. *tritici*). The test plants were then placed in a greenhouse at from 20° to 22° C. and from 75 to 80% relative humidity. After 7 days, the extent of powdery mildew development was determined.

The results show that, when used as a liquor containing the active ingredient in a concentration of 0.025 or 0.006%, compounds 3, 23, 24, 26, 27, 42, 57, 59, 74, 84, 101, 108, 142, 163, 165 and 170 have a better fungicidal action (about 97%) than the known comparative substances A and B (about 90%).

USE EXAMPLE 2

Action on powdery mildew of cucumbers (curative)

Young cucumber plants of the Chinesische Schlange variety, in the two-leaf stage, were sprayed with an aqueous conidial suspension of powdery mildew of the cucumber (*Erysiphe cichoracearum* and *Sphaerotheca fuliginea*). After 20 hours, these plants were sprayed to runoff with an aqueous spray liquor containing (dry basis) 80% of active ingredient and 20% of emulsifier, and were placed in a greenhouse at from 20° to 22° C. and 70–80% humidity. 21 days after application of the active ingredient, the extent of fungal infestation was determined.

The results show that, when used as a liquor containing the active ingredient in a concentration of 0.025%, compounds 1, 24, 59, 66, 72, 74, 75, 125, 154, 159 and 163 have a better fungicidal action (about 97%) than the known comparative active ingredient A (about 60%).

USE EXAMPLE 3

Action on wheat brown rust

Leaves of pot-grown wheat seedlings of the Frühgold variety were dusted with spores of brown rust (*Puccinia recondita*). The pots were then placed in a chamber at from 20° to 22° C. and with a high humidity (90–95%) for 24 hours. During this time, the spores germinated, and the germ tubes penetrated into the leaf tissue. The infected plants were then sprayed to runoff with aqueous spray liquors containing (dry basis) 80% of active ingredient and 20% of emulsifier. When the spray coating had dried on, the test plants were placed in a greenhouse at from 20° to 22° C. and from 65 to 70% relative humidity. After 8 days the extent of development of rust fungi on the leaves was determined.

The results show that, when used as a liquor containing the active ingredient in a concentration of 0.025%, compounds 1, 22, 26, 43, 71, 97, 147, 153, 169 and 170 have a better fungicidal action (about 90%) than the known comparative active ingredient A (about 50%).

USE EXAMPLE 4

Action on *Pyrenophora teres*

Leaves of pot-grown barley seedlings of the Asse variety, in the two-leaf stage, were sprayed to runoff with an aqueous spray liquor containing (dry basis) 80% of active ingredient and 20% of emulsifier. On the following day, the dried plants were inoculated with an aqueous spore suspension of *Pyrenophora teres*, and cultivated further for 7 days at from 17° to 19° C. and 95% relative humidity. The extent of fungal infestation was then determined.

The results show that, when used as a liquor containing the active ingredient in a concentration of 0.025%, the active ingredients 23, 42, 91, 98, 123, 124, 125 and 142 have a good fungicidal action (about 90%).

We claim:

1. An amine of the formula I

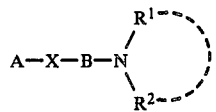

wherein

A is an unsubstituted or halosubstituted $C_3$–$C_{19}$-alkyl, a cycloalkyl or cycloalkenyl which is unsubstituted or mono- or polysubstituted by an alkyl of 1 to 4 carbon atoms, or a phenylalkyl which is unsubstituted or mono- or polysubstituted by a halogen or an alkyl of 1 to 4 carbon atoms, X is oxygen, B is an alkylene chain of 4 to 10 carbon atoms which is unsubstituted or mono- or polysubstituted by an alkyl of 1 to 4 carbon atoms, and —$NR^1R^2$ is a 2,6-dimethylmorpholino group, and salts thereof.

2. The amine of claim 1 wherein A is (4-tert.-butyl)-cyclohexane and B is butylene.

3. A fungicide comprising a solid or liquid carrier and, as the active ingredient, an effective amount of an amine of the formula I

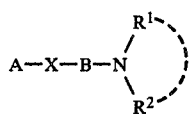

wherein

A is an unsubstituted or halosubstituted $C_3$–$C_{19}$-alkyl, a cycloalkyl or cycloalkenyl which is unsubstituted or mono- or polysubstituted by an alkyl of 1 to 4 carbon atoms, or a phenylalkyl which is unsubstituted or mono- or polysubstituted by a halogen or an alkyl of 1 to 4 carbon atoms, X is oxygen, B is an alkylene chain of 4 to 10 carbon atoms which is unsubstituted or mono- or polysubstituted by an alkyl of 1 to 4 carbon atoms, and —$NR^1R^2$ is a 2,6-dimethylmorpholino group, or a salt thereof.

4. The fungicide of claim 3 containing from 0.1 to 95% by weight of the active ingredient.

5. The fungicide of claim 3 further comprising a herbicide, an insecticide, a plant growth regulator, an additional fungicide or a fertilizer.

6. The fungicide of claim 4 wherein the amine is N-[4-(tert.-butyl)-cyclohexyloxybutyl]-2,6-dimethylmorpholine.

7. A method of controlling fungi comprising applying to the fungi or the materials, plants, soil or seeds to be protected from fungal infestation an effective fungicidal amount of an amine of the formula I

wherein

A is an alkyl or alkenyl which is unsubstituted or halosubstituted, a cycloalkyl or cycloalkenyl which is unsubstituted or mono- or polysubstituted by an alkyl of 1 to 4 carbon atoms, or a phenylalkyl or phenylalkenyl which is unsubstituted or mono- or polysubstituted by a halogen or an alkyl of 1 to 4 carbon atoms, X is oxygen, B is an alkylene chain of 2 to 10 carbon atoms which is unsubstituted or mono- or polysubstituted by an alkyl of 1 to 4 carbon atoms, and —$NR^1R^2$ is a morpholino, 2- or 3-methylmorpholino, 2,5-dimethylmorpholino or 2,6-dimethylmorpholino group or a salt or fungicidal composition thereof.

8. The method of claim 7 wherein a fungicidal composition comprising the amine or salt thereof and a solid or liquid carrier is applied to the fungi or the materials, plants, soil or seeds.

9. The method of claim 8 wherein the fungical composition is applied by spraying or dusting.

10. The method of claim 8 wherein the fungicidal composition further comprises a herbicide, an insecticide, a plant growth regulator, an additional fungicide or a fertilizer.

* * * * *